United States Patent [19]

Breuer et al.

[11] Patent Number: 4,762,922

[45] Date of Patent: Aug. 9, 1988

[54] 2-OXO-1-[[(SUBSTITUTED SULFONYL)AMINO]-CARBONYL]AZETIDINES

[75] Inventors: Hermann Breuer, Schoenhofen; Uwe D. Treuner, Etterzhausen, both of Fed. Rep. of Germany

[73] Assignee: Squibb Corporation, Princeton, N.J.

[21] Appl. No.: 70,286

[22] Filed: Jul. 1, 1987

[51] Int. Cl.$^4$ .............. A61K 31/395; A61K 31/425; A61K 31/44; C07D 705/08
[52] U.S. Cl. .................................. 540/363; 540/357; 540/360; 540/364
[58] Field of Search ............... 540/357, 360, 363, 364

[56] References Cited

U.S. PATENT DOCUMENTS 4,587,047 5/1986 Breuer et al. ............... 540/364

FOREIGN PATENT DOCUMENTS 0062876 10/1982 European Pat. Off. .
2181130 4/1987 United Kingdom .

OTHER PUBLICATIONS

Abstract No. 646 from 1984 ICAAC Meeting, "Antimicrobial Activities of 1-Carbacephem Compounds and Their Structure-Activity Relationships", Mochida et al.

Primary Examiner—Mark L. Berch
Attorney, Agent, or Firm—Lawrence S. Levinson; Donald J. Barrack

[57] ABSTRACT

Antibacterial activity is exhibited by 2-azetidinones having a 3-acylamino substituent and having an activating group in the 1-position of the formula

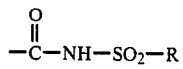

wherein R is

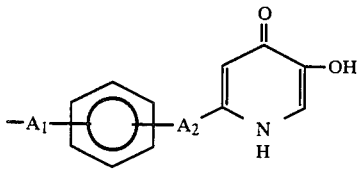

or

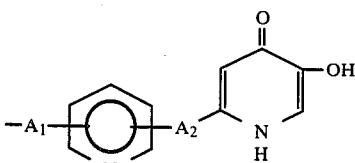

$A_1$ is —NH— or

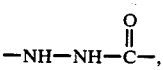

and $A_2$ is

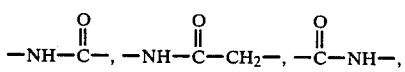

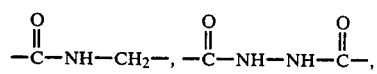

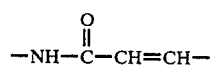

or —CH=CH—.

25 Claims, No Drawings

2-OXO-1-[[(SUBSTITUTED SULFONYL)AMINO]-CARBONYL]AZETIDINES

DESCRIPTION OF THE INVENTION

Compounds having the formula

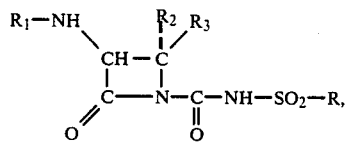  I and pharmaceutically acceptable salts thereof, exhibit antibacterial activity. In formula I, and throughout the specification, the symbols are as defined below.

R is

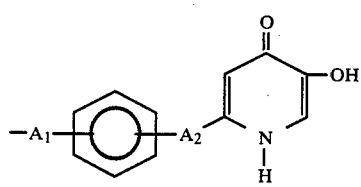

or

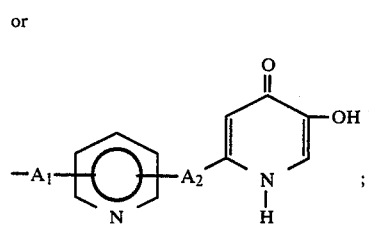

$R_1$ is an acyl group derived from a carboxylic acid; $R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

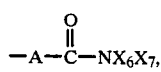

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

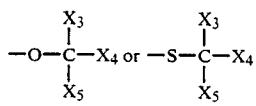

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

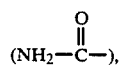

(substituted amino)carbonyl, or cyano (—C≡N)], or

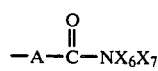

[wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

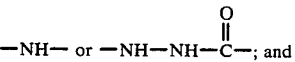

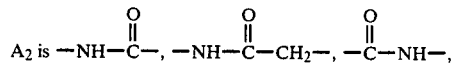

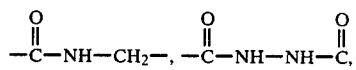

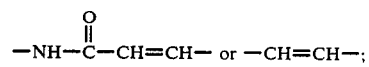

The above symbols (e.g., $A_1$, and $A_2$) are used to represent groups of multiple atoms. These groups are inserted in the structural formulas shown herein in the order in which they are presented (i.e., from left to right). For example, if R is

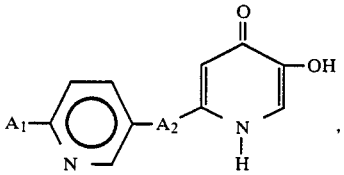

$A_1$ is —NH— and $A_2$ is

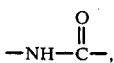

the R group would be

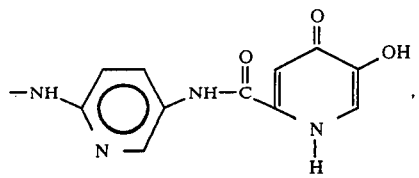

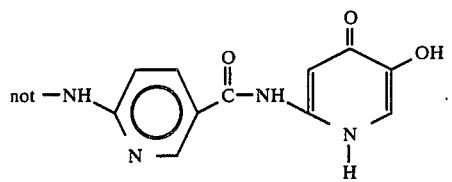

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloakyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino (—NH₂), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH₂), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

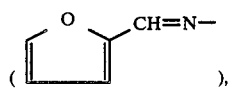

benzylideneamino and substituted alkyl groups (wherein the alkyl group has 1 to 4 carbons). One type of "4, 5, 6 or 7-membered heterocycle" is the heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino (—NH₂).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

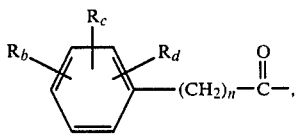

-continued

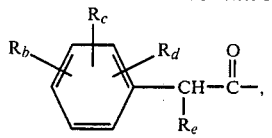

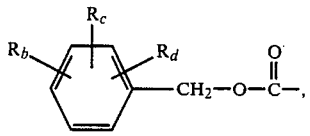

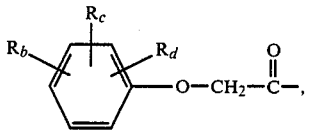

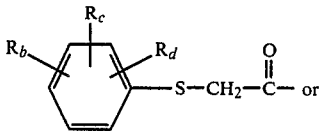

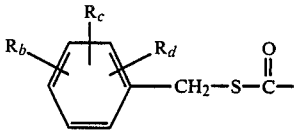 or wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thiomethyl]thio.

Preferred carbocyclic aromatic acyl groups include those having the formula

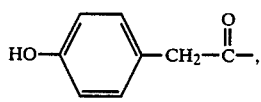

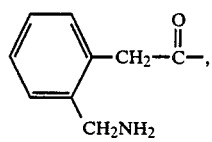

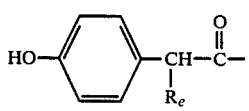

($R_e$ is preferably a carboxyl salt or sulfo salt) and

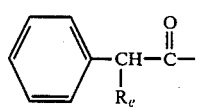

($R_e$ is preferably a carboxyl salt or sulfo salt).

(c) Heteroaromatic groups having the formula

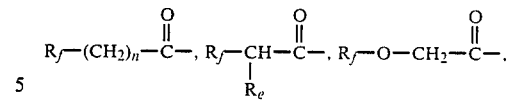

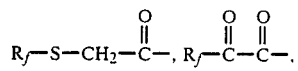

wherein n is 0, 1, 2 or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

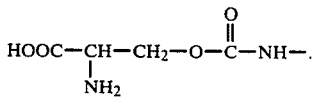

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

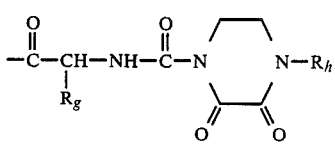

wherein $R_g$ is an aromatic group (including carbocyclic aromatics such as those of the formula

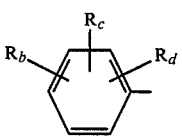

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

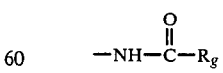

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oximino)arylacetyl groups having the formula $$-\overset{O}{\underset{\|}{C}}-\underset{\underset{R_g}{|}}{C}=N-O-R_i$$

wherein $R_g$ is as defined above and $R_i$ is hydrogen, alkyl, cycloalkyl, $$\underset{-C-COOH}{\overset{CH_2-(CH_2)_{1,2\ or\ 3},}{\diagdown\diagup}}$$

2-pyrrazolylmethyl, (2-oxo-3-pyrrolidinyl)methyl, alkylaminocarbonyl, arylaminocarbonyl (i.e., $$-\overset{O}{\underset{\|}{C}}-NH-R_g$$

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-ethyl, 1-carboxy-1-methylethyl, 2,2,2-trifluoroethyl, or 1-carboxycyclopropyl.

(f) (Acylamino)arylacetyl groups having the formula $$-\overset{O}{\underset{\|}{C}}-\underset{\underset{R_g}{|}}{CH}-NH-\overset{O}{\underset{\|}{C}}-R_j$$

wherein $R_g$ is as defined above and $R_j$ is

[structure with $R_b$, $R_c$, $R_d$ substituents and $(CH_2)_n$—O—], amino, alkylamino, (cyanoalkyl)amino, amido, alkylamido, (cyanoalkyl)amido, $$-CH_2-NH-\overset{NH}{\underset{\|}{C}}-\text{[pyridyl]}, \quad -\underset{\underset{|}{NH_2}}{CH}-CH_2-\overset{O}{\underset{\|}{C}}-NH-CH_3,$$

[pyridinol structure]—SO$_2$—N(CH$_2$—CH$_2$—OH)$_2$,

[HO-pyridyl-CH$_3$ structure], [OH-naphthyridine structure],

[OH-pyrido-pyrimidinyl-piperazinyl-N—CHO structure], or

[HO, HO-chromone-C(=O)— structure]

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula $$-\overset{O}{\underset{\|}{C}}-\underset{\underset{R_g}{|}}{CH}-NH-\overset{O}{\underset{\|}{C}}-\underset{\underset{CH_2-CH_2}{|}}{N}\diagdown\underset{\diagup}{\overset{\overset{O}{\|}}{C}}N-R_k$$

wherein $R_g$ is as defined above and $R_k$ is hydrogen, alkylsulfonyl, arylmethyleneamino (i.e., —N=CH—$R_g$ wherein $R_g$ is as defined above), $$-\overset{O}{\underset{\|}{C}}-R_m$$

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C). Also included within the scope of this invention are racemic mixtures which contain the above-described β-lactams.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

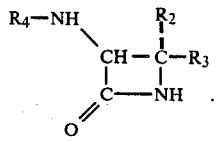   II

In formula II, and throughout the specification, the symbol "$R_4$" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate having the formula

   III wherein Y is a leaving group such as chlorine, yields the corresponding compound having the formula

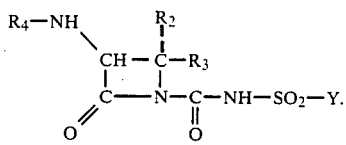   IV

The reaction is preferably run in an inert organic solvent, e.g., ethyl acetate, tetrahydrofuran, dimethoxyethane, dichloromethane, acetonitrile or mixtures of these solvents. Displacement of the leaving group "Y" with the desired group "R" can be accomplished using the appropriate nucleophile having the formula

RH   V optionally in the presence of a base (e.g., triethylamine), and yields the corresponding compound having the formula

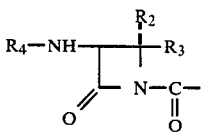   VI

Alternatively, the displacement of the leaving group can be accomplished by reaction of a compound of formula IV with a protected form of a compound of formula V. Following the displacement reaction, the protecting groups can be removed using art-recognized techniques to yield a compound of formula VI.

Protected forms of a compound of formula V, and of all reactants described herein which contain a 3-hydroxy-4-pyridone moiety, include those compounds wherein the hydroxyl group is protected, those compounds wherein the hydroxyl group and the ring nitrogen are protected, and those compounds wherein both pyridone oxygens are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis. If acyl is used, later deprotection can be accomplished by hydrolysis.

Deprotection of a compound of formula VI using conventional techniques yields the corresponding key intermediate having the formula

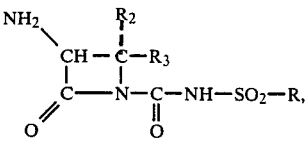   VII or a salt thereof. The particular deprotection reaction used will, of course, depend on the protecting group ("$R_4$") present. If, for example, $R_4$ is a t-butoxycarbonyl protecting group, deprotection can be accomplished by treatment of a compound of formula VI with acid (e.g., formic acid or trifluoroacetic acid). If, for example, $R_4$ is a benzyloxycarbonyl protecting group, deprotection can be accomplished by catalytic hydrogenation of a compound of formula VI. Alternatively, the $R_4$ protecting group can be removed simultaneously with the other pyridone protecting groups immediately following the above-described displacement reaction.

Well known acylation techniques can be used to convert an intermediate of formula VII to a corresponding product of formula I. Exemplary techniques include reaction of a compound of formula VII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

An alternative procedure for preparing the compounds of formula I comprises first acylating (acylation techniques have been described above) a 3-amino-2-azetidinone having the formula

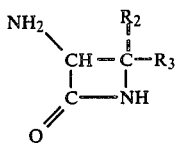
VIII to yield an intermediate having the formula

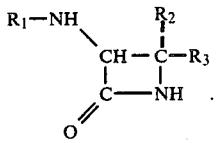
IX

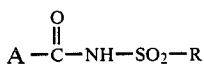

activating group can be introduced in the 1-position of a compound of formula IX (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

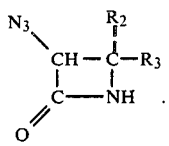
X

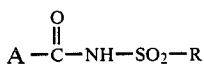

activating group can be introduced in the 1-position of a compound of formula X (using the procedures described above) to obtain the corresponding compound having the formula

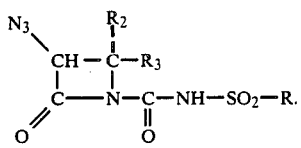
XI

Reduction of an intermediate of formula XI yields the corresponding intermediate having the formula

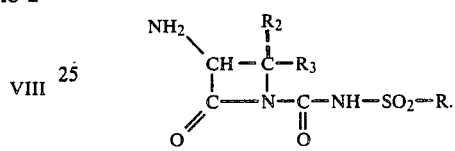
VII

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula X can be reduced to the corresponding 3-amino-2-azetidinone having the formula

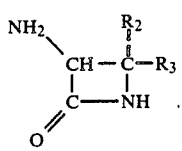
VIII

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce a

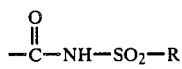

activating group in the 1-position) to yield the products of formula I.

Still another synthesis for preparing the compounds of formula I wherein $R_2$ and $R_3$ are each hydrogen utilizes a 6-acylaminopenicillanic acid having the formula

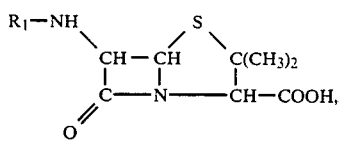  XII

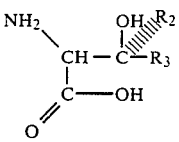  XV or a salt thereof, as the starting material. By adapting procedures described in the literature, 3-acylamino-2-azetidinone can be obtained from the corresponding 6-acylaminopenicillanic acid of formula XII: see, for example, *Chem. Soc. Special Publication* No. 28, pg. 228 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

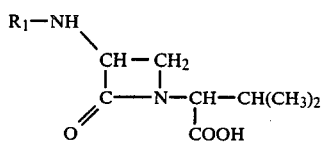  XIII by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

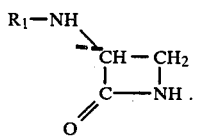  XIV

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

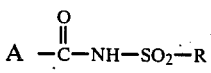

activating group can be introduced in the 1-position of a compound of formula XIV (yielding products of formula I wherein $R_2$ and $R_3$ are each hydrogen) using the procedures described above.

Still another variation of the above-described synthetic routes for preparing a compound of formula I wherein $R_2$ and $R_3$ are each hydrogen comprises first desulfurizing 6-aminopenicillanic acid, acylating the resulting compound to yield a compound of formula XIII and then proceeding as described above to obtain first a 3-acylamino-2-azetidinone of formula XIV and then a product of formula I.

The azetidinones of formula I can also be prepared from amino acids having the formula The amino group is first protected (with a protecting group "$R_4$", e.g., t-butoxycarbonyl). The carboxyl group of the protected amino acid is then reacted with an amine having the formula

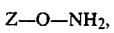  XVI wherein Z is alkyl, benzyl or triphenylmethyl, in the presence of a carbodiimide to yield a compound having the formula

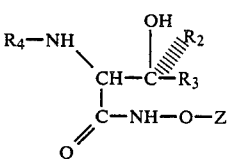  XVII

The hydroxyl group of a compound of formula XVII is converted to a leaving group ("OL") with a reagent, such as methanesulfonyl chloride or pyridine-$SO_3$ complex.

The fully protected compound having the formula

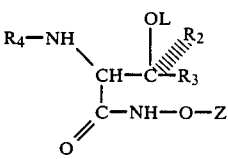  XVIII is cyclized by treatment with base, e.g., potassium carbonate. The reaction is preferably carried out in an organic solvent or an organic solvent/water mixture under reflux conditions, and yields a compound having the formula

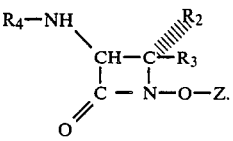  XIX

Alternatively, cyclization of a compound of formula XVII can be accomplished without first converting the hydroxyl group to a leaving group. Treatment of a compound of formula XVII with triphenylphosphine and diethylazodicarboxylate, yields a compound of formula XIX.

Exemplary procedures for the conversion of a compound of formula XVIII to a compound of formula XIX are described in *J. Amer. Chem. Soc.*, 102, 7026 (1980) and *J. Org. Chem.*, 47, 5160 (1982).

Both of the methods disclosed above for ring closure of a compound of formula XVII result in the inversion of the stereochemistry at the carbon atom bearing the $R_2$ and $R_3$ substituents when $R_2$ and $R_3$ are not the same.

Removal of the protecting group from the 1-position of an azetidinone of formula XIX can be accomplished via sodium reduction when Z is alkyl, and yields an intermediate having the formula

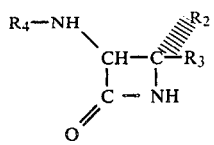

(at least one of $R_2$ and $R_3$ is hydrogen). If Z is benzyl, catalytic (e.g., palladium on charcoal) hydrogenation will initially yield the corresponding N-hydroxy compound, which upon treatment with titanium trichloride yields an intermediate of formula II. If Z is triphenylmethyl, formic acid or 70% acetic acid/water will initially yield the corresponding N-hydroxy compound.

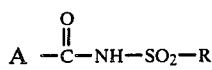

activating group can be introduced in the 1-position of a compound of formula II using the procedures described above, and the resulting compound can be deprotected and acylated.

The nucleophiles of formula V wherein R is

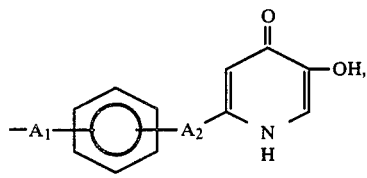

$A_1$ is —NH— and $A_2$ is

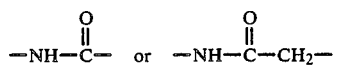

can be prepared by reacting a nitroaniline compound having the formula

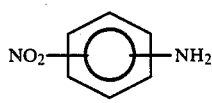

with an activated, suitably protected derivative of a carboxylic acid having the formula

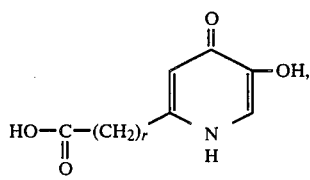

wherein r is 0 or 1, to yield, upon deprotection and reduction, the corresponding compound having the formula

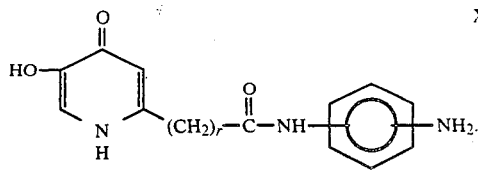

The nucleophiles of formula V wherein R is

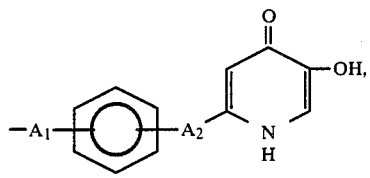

$A_1$ is

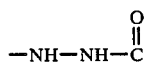

and $A_2$ is

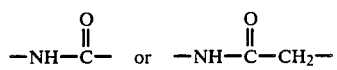

can be prepared by reacting monoprotected hydrazine with a nitrobenzoic acid having the formula

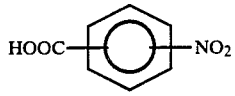

to obtain a compound having the formula

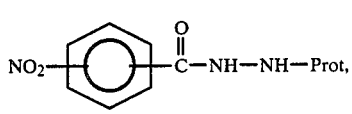

wherein Prot is a conventional amino protecting group. Reduction of a compound of formula XXIV to yield the corresponding amino compound, followed by reaction with an activated, suitably protected carboxylic acid of formula XXI yields, upon deprotection, the corresponding compound having the formula

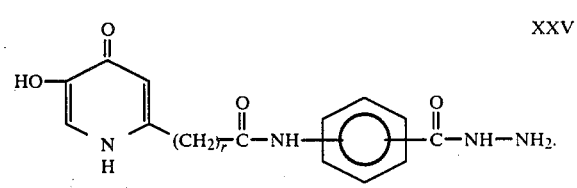

The nucleophiles of formula IV wherein R is

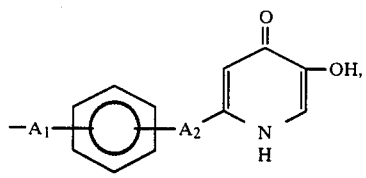

A₁ is —NH—, and A₂ is

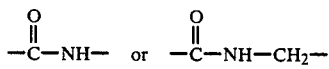

can be prepared by reacting a nitrobenzoic acid of formula XXIII with a suitably protected derivative of a compound having the formula

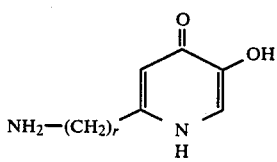 XXVI to yield, after reduction and deprotection, the corresponding compound having the formula

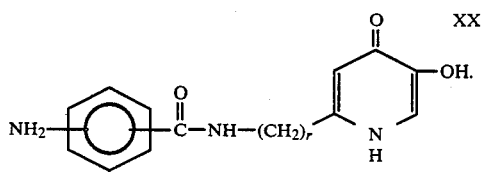 XXVII

The nucleophiles of formula V wherein R is

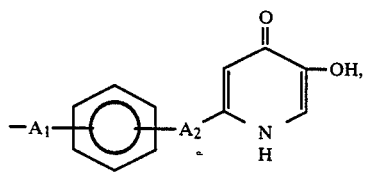

A₁ is

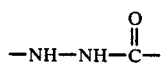

and A₂ is

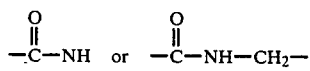

can be prepared by reacting a dicarboxylic acid having the formula

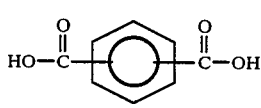 XXVIII with monoprotected hydrazine to obtain the corresponding compound having the formula

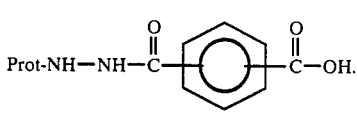 XXIX

Reaction of a compound of formula XXIX with a suitably protected derivative of a compound of formula XXVI, followed by deprotection yields the corresponding compound having the formula

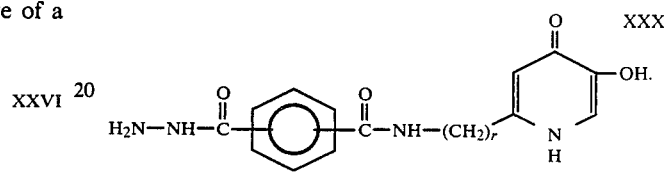 XXX

The nucleophiles of formula V wherein R is

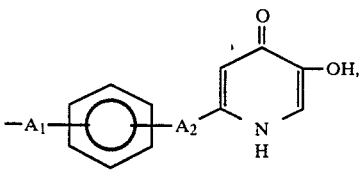

A₁ is —NH—, and A₂ is

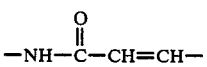

can be prepared by reacting a nitroaniline of formula XX with a suitably protected carboxylic acid having the formula

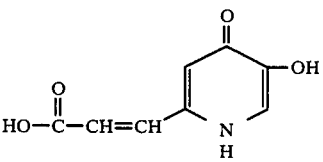 XXXI to yield, after selective reduction (using, for example, sodium dithionate) and deprotection, the corresponding compound having the formula

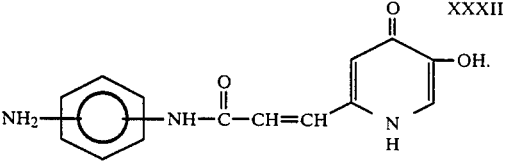 XXXII

The nucleophiles of formula V wherein R is

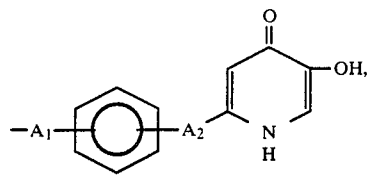

$A_1$ is

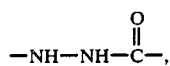

and $A_2$ is

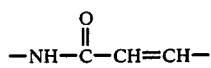

can be prepared by first reducing a compound of formula XXIV to the corresponding amino compound and then reacting that compound with a compound of formula XXXI to yield, upon deprotection, the corresponding compound having the formula

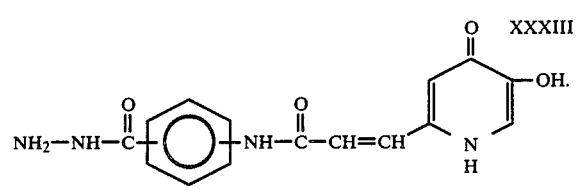
XXXIII

The nucleophiles of formula V wherein R is

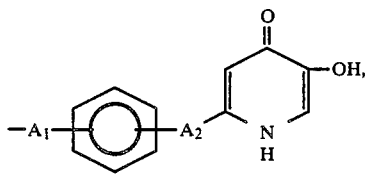

$A_1$ is —NH— and $A_2$ is

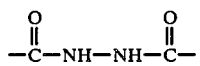

can be prepared by first deprotecting a compound of formula XXIV and then reacting the deprotected compound with an activated, suitably protected derivative of a carboxylic acid having the formula

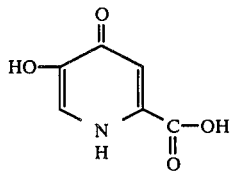
XXXIV to yield, upon reduction and deprotection, the corresponding compound having the formula

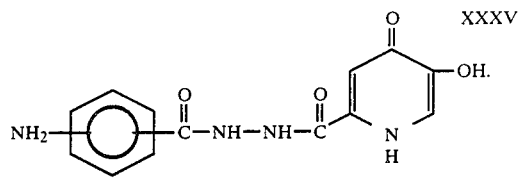
XXXV

The nucleophiles of formula V wherein R is

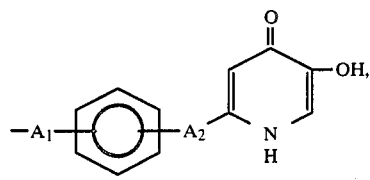

$A_1$ is

and $A_2$ is

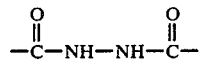

can be prepared by reacting a compound of formula XXIX with a suitably protected derivative of a compound having the formula

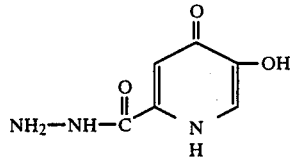
XXXVI to yield, upon deprotection, the corresponding compound having the formula

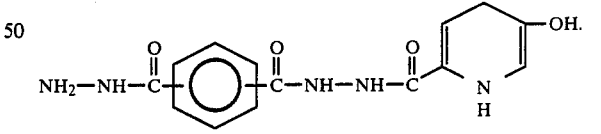
XXXVII

The nucleophiles of formula V wherein R is

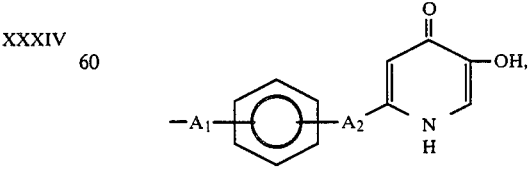

$A_1$ is —NH— and $A_2$ is —CH=CH— can be prepared by performing the Wittig reaction of a compound having the formula

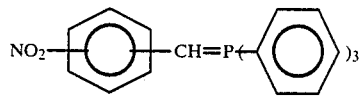

XXXVIII with a suitably protected derivative of an aldehyde having the formula

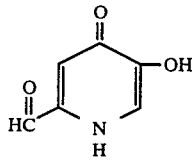

IXL to yield, upon selective reduction of the nitro group followed by deprotection, the corresponding compound having the formula

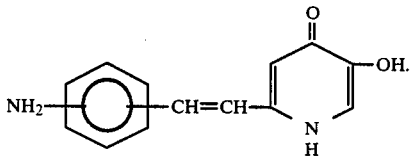

XL

The nucleophiles of formula V wherein R is

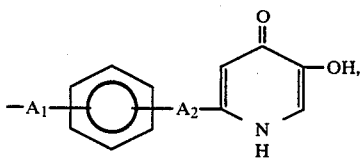

$A_1$ is

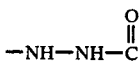

and $A_2$ is —CH=CH— can be prepared by performing the Wittig reaction of a protected derivative of a compound having the formula

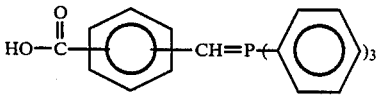

XLI with a suitably protected derivative of an aldehyde of formula IXL to yield a protected derivative of the corresponding compound having the formula

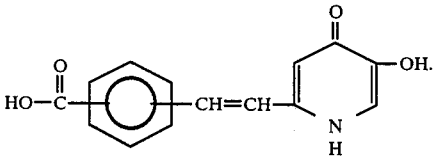

XLII

Deprotection of a compound of formula XLII, followed by reaction with a monoprotected hydrazine yields, upon deprotection, the corresponding compound having the formula

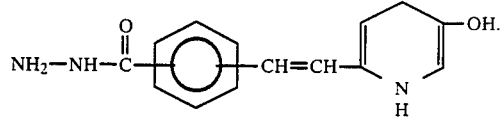

XLIII

The nucleophiles of formula V wherein R is

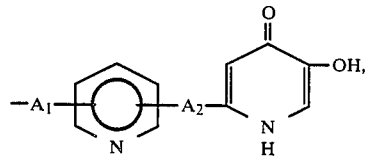

$A_1$ is —NH— and $A_2$ is

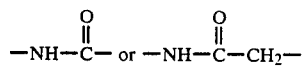

can be prepared by reacting a diaminopyridine compound having the formula

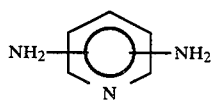

XLIV with an activated, suitably protected derivative of a carboxylic acid of formula XXI to yield, upon deprotection, the corresponding compound having the formula

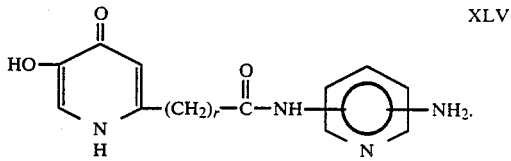

XLV

The nucleophiles of formula V wherein R is

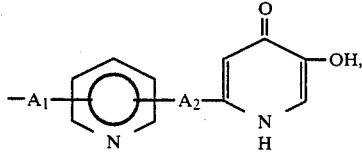

$A_1$ is

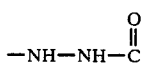

and $A_2$ is

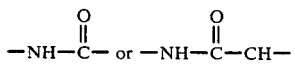

can be prepared by reacting an activated, suitably protected derivative of a compound of formula XXI with a compound having the formula

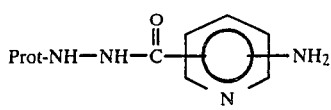 XLVI to yield, upon deprotection, the corresponding compound having the formula

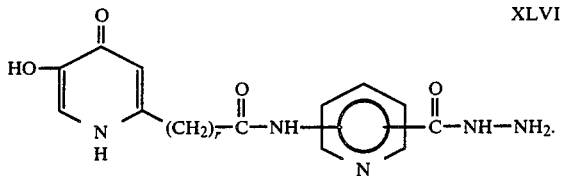 XLVII

The nucleophiles of formula V wherein R is

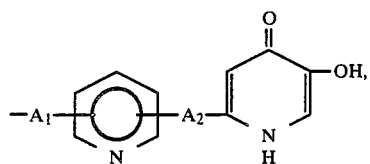

$A_1$ is —NH— and $A_2$ is

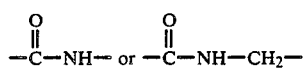

can be prepared by reacting a suitably protected derivative of a compound of formula XXVI with a compound having the formula

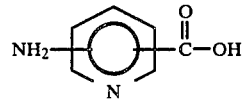 XLVIII to yield, after deprotection, the corresponding compound having the formula

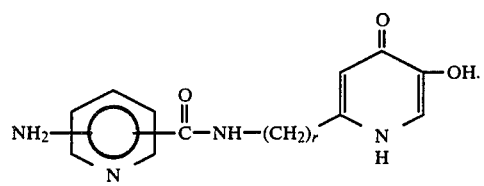 IL

The nucleophiles of formula V wherein R is

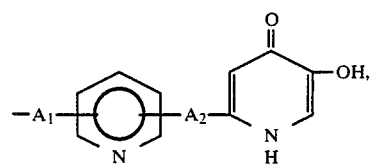

$A_1$ is

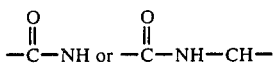

and $A_2$ is

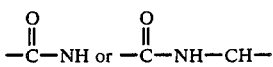

can be prepared by reacting a suitably protected derivative of a compound of formula XXVI with a compound having the formula

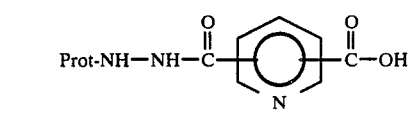

to obtain, upon deprotection, the corresponding compound having the formula

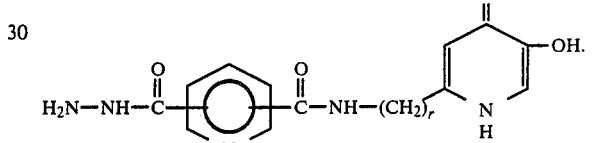 L

The nucleophiles of formula V wherein R is

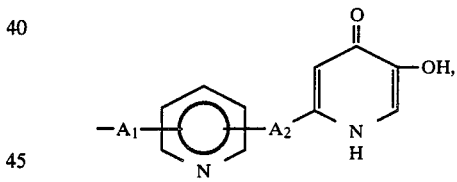

$A_1$ is —NH—, and $A_2$ is

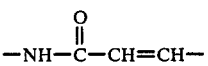

can be prepared by reacting a compound having the formula

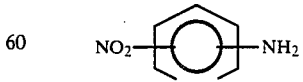 LI with a suitably protected derivative of a carboxylic acid of formula XXXI to yield, after selective reduction (using, for example, sodium dithionate) and deprotection, the corresponding compound having the formula

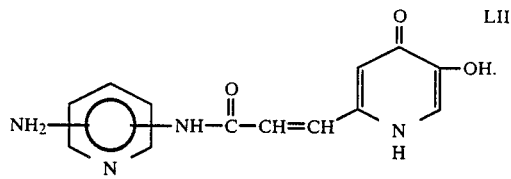

LII

The nucleophiles of formula V wherein R is

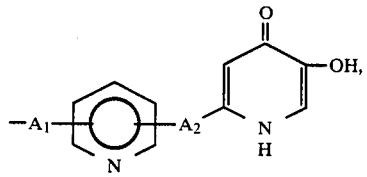

A₁ is

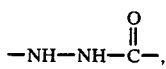

and A₂ is

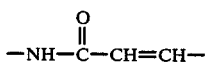

can be prepared by reacting a compound of formula XLVI with a suitably protected derivative of a compound of formula XXXI to yield, upon deprotection, the corresponding compound having the formula

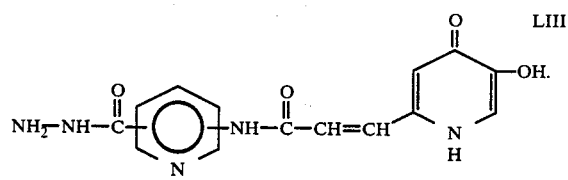

LIII

The nucleophiles of formula V wherein R is

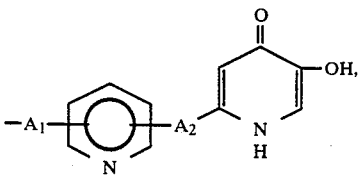

A₁ is —NH— and A₂ is

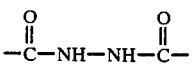

can be prepared by reacting a compound having the formula

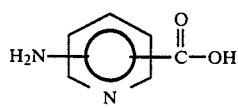

LIV with an activated, suitably protected derivative of a carboxylic acid of formula XXXVI to yield, upon deprotection, the corresponding compound having the formula

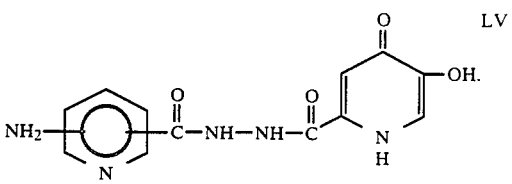

LV

The nucleophiles of formula V wherein R is

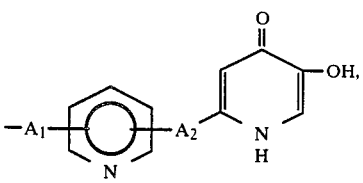

A₁ is

and A₂ is

can be prepared by reacting a compound having the formula

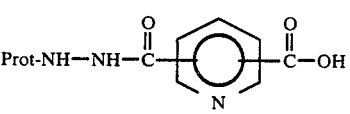

LVI with an activated, suitably protected derivative of a compound of formula XXXVI to yield, upon deprotection, the corresponding compound having the formula

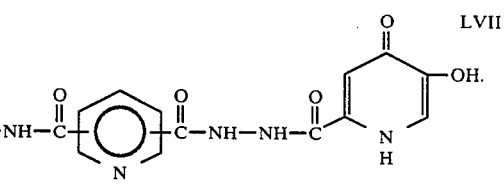

LVII

The nucleophiles of formula V wherein R is

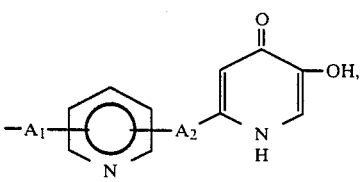

$A_1$ is —NH— and $A_2$ is —CH=CH— can be prepared by performing the Wittig reaction of a compound having the formula

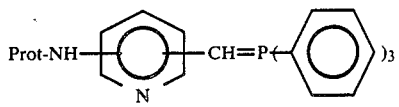
LVIII with a suitably protected derivative of an aldehyde of formula IXL to yield, upon deprotection, the corresponding compound having the formula

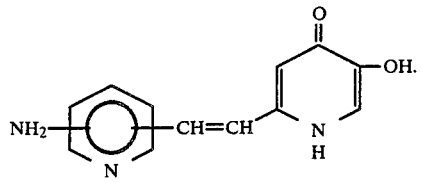
LIX

The nucleophiles of formula V wherein R is

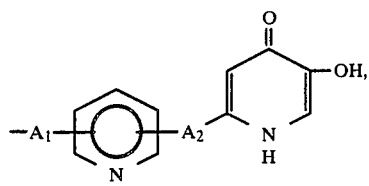

$A_1$ is

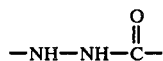

and $A_2$ is —CH=— can be prepared by performing the Wittig reaction of a protected derivative of a compound having the formula

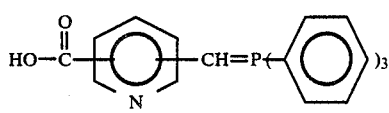
LX with a suitably protected derivative of an aldehyde of formula IXL to yield a protected derivative of the corresponding compound having the formula

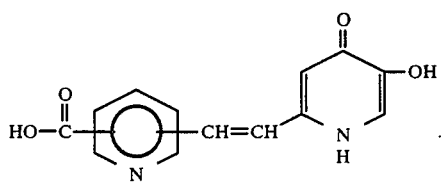
LXI

Deprotection of a compound of formula LXI, followed by reaction with monoprotected hydrazine yield, upon deprotection, the corresponding compound having the formula

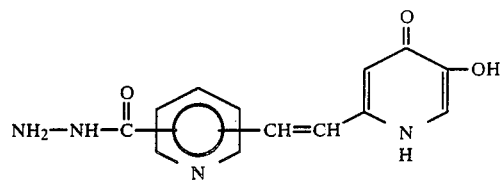
LXII

Alternatively, the compounds of this invention can be prepared by first reacting a compound of formula IV with a compound having the formula

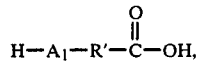
LXIII wherein R'

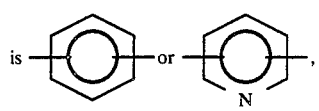

in the presence of base or N-methyl-N-(trimethylsilyl)-trifluoroacetamide to obtain a compound having the formula

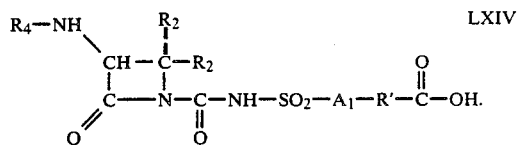
LXIV

Reaction of a compound of formula LXIV with a suitably protected derivative of a compound of the formula

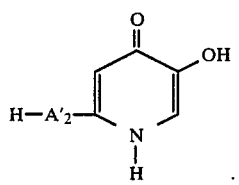
LXV wherein $A'_2$ is —NH—, —NH—CH$_2$— or

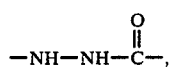

yields upon deprotection and acylation, the corresponding product of formula I wherein $A_2$ is

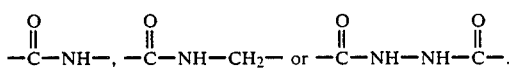

A compound of formula IV can also be reacted with a compound having the formula

H—$A_1$—R'—NH—Prot    LXVI in the presence of base or N-methyl-N-(trimethylsilyl)-trifluoroacetamide to yield, upon deprotection, the corresponding compound having the formula $$R_4-NH \quad R_2 \atop CH-C-R_3 \atop C-N-C-NH-SO_2-A_1-R'-NH_2 \atop O$$ LXVII Reaction of a compound of formula LXVII with a suitably protected derivative of a compound of the formula

LXVIII (pyridinone structure with OH, HO—A''$_2$—, and =O substituents)

wherein A''$_2$ is $$-\overset{O}{\underset{\|}{C}}-, \ -\overset{O}{\underset{\|}{C}}-CH_2- \ \text{or} \ -\overset{O}{\underset{\|}{C}}-CH=CH-,$$

yields upon deprotection and acylation, the corresponding product of formula I wherein A$_2$ is $$-NH-\overset{O}{\underset{\|}{C}}-, \ -NH-\overset{O}{\underset{\|}{C}}-CH_2- \ \text{or} \ -NH-\overset{O}{\underset{\|}{C}}-CH=CH-.$$

The compounds described herein are pictured with the organic group (pyridinone structure with OH and =O)

This group exists in a tautomeric equilibrium with a group of the formula (pyridine structure with two OH groups)

Depending on the additional substituent to the group, one form or the other will predominate. Both forms are meant to be included herein.

The following examples are specific embodiments of this invention.

EXAMPLE 1

[3S(Z)]-2-[[[1-(2-Amino-4-thiazolyl)-2-[[1-[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]amino]-2-oxoethylidene]amino]oxy]-2-methylpropanoic acid, disodium salt

(A)

N-[[1,4-Dihydro-4-oxo-5-(phenylmethoxy)-1-(phenylmethyl)-2-pyridinyl]methyl]-4-nitrobenzamide To a suspension of 10.7 g (0.03 mol) of N-[[1,4-dihydro-4-oxo-5-(phenylmethoxy)-1-(phenylmethyl)-2-pyridinyl]methyl]amine in 100 ml of dichloromethane was added 8.96 ml of triethylamine (0.064 mol). A turbid brownish solution was formed, to which, with cooling, a solution of 5.57 g (0.03 mol) of 4-nitrobenzoyl chloride in 20 ml dichloromethane was added dropwise. The solution was stirred for 4 hours at room temperature, evaporated in vacuo and triturated with water to form 15.7 g of crude material, which was added to 100 ml of boiling ethanol. The pure compound crystallized from the boiling solution. Yield: 9.0 g of N-[[1,4-dihydro-4-oxo-5-(phenylmethoxy)-1-(phenylmethyl)-2-pyridinyl]methyl]-4-nitrobenzamide, melting point 188°–190° C.

NMR (DMSO-d$_6$): $\delta$=4.37 (d, 2H); 5.06 (s, 2H); 5.18 (s, 2H); 6.20 (s, 1H); 6.91–7.30 (m, 5H); 7.38 (m, 5H); 7.72 (s, 1H); 8.04 (d, 2H); 8.30 (d, 2H); 9.30 (t, 1H).

(B)

4-Amino-N-[(1,4-dihydro-5-hydroxy-4-oxo-2-pyridinyl)methyl]benzamide, trifluoroacetate salt To a suspension of 8.5 g of 4-nitrobenzoyl chloride in 150 ml of dimethylformamide was added 6.93 ml of trifluoroacetic acid to form a solution. 4.5 Grams of palladium on charcoal (10%) was added and hydrogen was passed through the stirred suspension for two hours. After filtration, the filtrate was evaporated in vacuo and the residue triturated with ether to form 5.7 g of 4-amino-N-[(1,4-dihydro-5-hydroxy-4-oxo-2-pyridinyl)methyl]benzamide, trifluoroacetate salt.

NMR (DMSO-d$_6$): $\delta$=4.54 (m, 2H); 6.60 (d, 2H); 7.08 (s, 1H); 7.67 (d, 2H); 8.07 (s, 1H); 8.67–9.68 (m broad; 2×NH, NH$_2$, OH=5H).

(C)

(S)-[1-[[[[4-[[[(1,4-Dihydro-5-hydroxy-4-oxo-2-pyridinyl)methyl]amino]carbonyl]phenyl]amino]sulfonyl]amino]carbonyl]-2-oxo-3-azetidinyl]carbamic acid, phenylmethyl ester To a suspension of 1.87 g of 4-amino-N-[(1,4-dihydro-5-hydroxy-4-oxo-2-pyridinyl)methyl]benzamide, trifluoroacetate salt (0.005 mol) in 20 ml of ethyl acetate was added 2.78 ml of N-methyl-N-(trimethylsilyl)trifluoroacetamide (0.015 mol). After 10 minutes, a solution was formed (solution A).

To a suspension of 1.1 of (S)-3-[[(phenylmethoxy)carbonyl]amino]-2-azetidinone (0.005 mol) in 20 ml of ethyl acetate was added 0.44 ml (0.005 mol) of chlorosulfonylisocyanate to form a solution. The solution was stirred for 1 hour, then 2.09 ml of triethylamine (0.015 mol) and 20 ml of dichloromethane were added, with cooling, followed by solution A. The mixture was stirred overnight at room temperature and evaporated in vacuo. The residue was dissolved in a mixture from acetone and water and the pH of the mixture was adjusted to 6–6.5 by the addition of 2N sodium hydroxide with cooling. After stirring for 2 hours, the acetone was removed in vacuo and the remaining aqueous phase was lyophilized. The crude sodium salt of (S)-[1-[[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]carbamic acid, phenylmethyl ester was purified by MPLC on XAD-2. The compound was eluted with water. The fractions containing pure compound (TLC) were collected, evaporated to a small volume and acidified to precipitate (S)-[1-[[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]carbamic acid, phenylmethyl ester. The precipitate was isolated by filtration. Yield: 0.9 g of (S)-[1-[[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]carbamic acid, phenylmethyl ester.

IR (KBr): 1775 ($\beta$-lactam).

NMR (DMSO-d$_6$+CF$_3$COOH): $\delta$=3.56 (dd, 1H); 3.80 (dd, 1H); 4.55 (s, 2H); 7.79 (dd, 1H); 5.00 (s, 2H); 7.15 (s, 1H); 7.30 (d, 2H); 7.32 (s, 5H); 7.85 (d, 2H); 8.05 (s, 1H).

(D)

(S)-3-Amino-N-[[[4-[[[(1,4-dihydro-5-hydroxy-4-oxo-2-pyridinyl)methyl]amino]carbonyl]phenyl]amino]sulfonyl]-2-oxo-1-azetidinecarboxamide, trifluoroacetate salt 1.2 Grams of (S)-[1-[[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]-carbamic acid, phenylmethyl ester was added, at 10° C., to a mixture of 5 ml of trifluoroacetic acid and 1 of ml thioanisole. The solution was stirred overnight at 10° C. and evaporated in vacuo at room temperature. To the oily residue, 20 ml of ethyl acetate was added followed by 30 ml of ether. The precipitate was isolated by filtration. Yield: 1.1 g of crude (S)-3-amino-N-[[[4-[[[(1,4-dihydro-5-hydroxy-4-oxo-2-pyridinyl)methyl]amino]-carbonyl]phenyl]amino]sulfonyl]-2-oxo-1-azetidine-carboxamide, 1,0-trifluoroacetate salt.

IR (KBr): 1790 ($\beta$-lactam).

(E)

[3S(Z)]-2-[[[1-(2-Amino-4-thiazolyl)-2-[[1-[[[[4-[[[(1,4-dihydro-5-hydroxy-4-oxo-2-pyridinyl)methyl]amino]-carbonyl]phenyl]amino]sulfonyl]amino]carbonyl]-2-oxo-3-azetidinyl]amino]-2-oxoethylidene]amino]oxy]-2-methylpropanoic acid, diphenylmethyl ester To a suspension of 0.88 g (0.002 mol) of (Z)-2-amino-$\alpha$-[[2-diphenylmethoxy)-1,1-dimethyl-2-oxoethoxy]imino]-4-thiazoleacetic acid in 30 ml of acetonitrile was added, at $-30°$ C., 0.84 ml of triethylamine (0.006 mol) followed by 0.44 ml of diphenyl chlorophosphate (0.002 mol) at the same temperature. The reaction mixture was stirred at $-30°$ C. for 1½ hours (solution A).

To a suspension of 1.1 g (0.002 mol) of (S)-3-amino-N-[[[4-[[[(1,4-dihydro-5-hydroxy-4-oxo-2-pyridinyl)methyl]amino]carbonyl]phenyl]amino]sulfonyl]-2-oxo-1-azetidinecarboxamide, trifluoroacetate salt in 30 ml of ethyl acetate was added, at room temperature, 1.6 ml of bistrimethylsilylacetamide (0.0066 mol). After stirring for 20 minutes, a clear solution was formed which was added to solution A at $-30°$ to $-25°$ C. The reaction mixture was stirred at $-10°$ C. for 1½ hours and at 0° C. for 1 hour and evaporated in vacuo. The remaining syrup was triturated with ice water. The solid product was isolated by filtration. Yield: 1.7 g of crude [3S(Z)]-2-[[[1-(2-amino-4-thiazolyl)-2-[[1-[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]amino]-2-oxoethylidene]amino]oxy]-2-methylpropanoic acid, diphenylmethyl ester.

IR (KBr): 1776 ($\beta$-lactam).

(F)

[3S(Z)]-2-[[[1-(2-Amino-4-thiazolyl)-2-[[1-[[[[4-[[[(1,4-dihydro-5-hydroxy-4-oxo-2-pyridinyl)methyl]amino]-carbonyl]phenyl]amino]sulfonyl]amino]carbonyl]-2-oxo-3-azetidinyl]amino]-2-oxoethylidene]amino]oxy]-2-methylpropanoic acid, disodium salt 1.7 Grams of [3S(Z)]-2-[[[1-(2-amino-4-thiazolyl)-2-[[1-[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]-amino]-2-oxoethylidene]amino]oxy]-2-methylpropanoic acid, diphenylmethyl ester was added to a mixture of 17 ml of trifluoroacetic acid and 3.5 ml of anisole. The mixture was stirred for 1 hour at $-10°$ C. Ether was added at $-10°$ C. to precipitate [3S(Z)]-2-[[[1-(2-amino-4-thiazolyl)-2-[[1-[[[[4-[[[(1,4-dihydro-5-hydroxy-4-oxo-2-pyridinyl)methyl]-amino]carbonyl]phenyl]amino]sulfonyl]amino]carbonyl]-2-oxo-3azetidinyl]amino]-2-oxoethylidene]amino]oxy]-2-methylpropanoic acid, trifluoroacetate. Yield: 1.2 g of crude material. The crude compound was dissolved in a mixture of 30 ml of water and 20 ml of acetone and the pH of the solution was adjusted to 5.5–6 by the addition of 2N sodium hydroxide. The acetone was removed in vacuo and the remaining aqueous solution was lyophilized to yield 1.1 g of crude compound. The crude material was purified by chromatography on XAD-2 (elution with water). Yield: 0.22 g of pure [3S(Z)]-2-[[[1-(2-amino-4-thiazolyl)-2-[[1-[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]amino]-2-oxoethylidene]amino]oxy]-2-methylpropanoic acid, disodium salt.

IR (KBr): 1770 ($\beta$-lactam).

NMR (DMSO-d$_6$+CF$_3$COOH): $\delta$=1.47 (s, 6H); 3.70 (dd, 1H); 3.90 (dd, 1H); 4.57 (s, 2H); 5.07 (dd, 1H); 6.99 (s, 1H); 7.14 (s, 1H); 7.32 (d, 2H); 7.89 (d, 2H); 8.05 (s, 1H).

EXAMPLE 2

[3S(Z)]-2-[[[1-(2-Amino-4-thiazolyl)-2-[[1-[[[[5-[[(1,4-dihydro-5-hydroxy-4-oxo-2-pyridinyl)carbonyl]amino]-2-pyridinyl]amino]sulfonyl]amino]carbonyl]-2-oxo-3-azetidinyl]amino]-2-oxoethylidene]amino]oxy]-2-methylpropanoic acid, disodium salt (A)

N-(6-Amino-3-pyridinyl)-4,5-bis(phenylmethoxy)-2-pyridinecarboxamide

To 7.28 g of 2,5-diaminopyridine, hydrochloride dissolved in 80 ml of dichloromethane and 40 ml of acetonitrile were added 22.3 ml of triethylamine and at 0°–5° C. a solution of 7.5 g of 4,5-bis(phenylmethoxy)-2-pyridinecarboxylic acid chloride in 20 ml of dichloromethane was added dropwise. After continuous stirring overnight, the precipitate was filtered off and washed with 20 ml of dichloromethane. The filtrate and the washed solution, both combined, were evaporated yielding 11.3 g of solid material. This was stirred with 100 ml of water, filtered off and dried. Purification by column chromatography on silica, eluting with ethyl acetate and then ethyl acetate/methanol (95:5) gave 5 g of N-(6-amino-3-pyridinyl)-4,5-bis(phenylmethoxy)-2-pyridinecarboxamide from fractions 138-215 (each 20 ml).

(B)
(S)-[1-[[[[[5-[[[4,5-Bis(phenylmethoxy)-2-pyridinyl]carbonyl]amino]-2-pyridinyl]amino]sulfonyl]amino]carbonyl]-2-oxo-3-azetidinyl]-carbamic acid, phenylmethyl ester 0.31 g of (S)-3-[[(phenylmethoxy)carbonyl]amino]-2-azetidinone and 0.12 ml of chlorosulfonyl isocyanate were stirred for one hour at room temperature in 200 ml of ethyl acetate. At 0° C., 0.59 ml of triethylamine was added followed by 0.6 g of N-(6-amino-3-pyridinyl)-4,5-bis(phenylmethoxy)-2-pyridinecarboxamide. After stirring overnight at room temperature and addition of 25 ml dichloromethane crystals of crude (S)-[1-[[[[[5-[[[4,5-bis(phenylmethoxy)-2-pyridinyl]-carbonyl]amino]-2-pyridinyl]amino]sulfonyl]amino]carbonyl]-2-oxo-3-azetidinyl]carbamic acid, phenylmethyl ester crystallized out. Purification of (S)-[1-[[[[[5-[[[4,5-bis(phenylmethoxy)-2-pyridinyl]carbonyl]amino]-2-pyridinyl]amino]sulfonyl]amino]carbonyl]-2-oxo-3-azetidinyl]-carbamic acid, phenylmethyl ester: column chromatography on HP-20 resin water/acetone gradient as eluent. Fractions 200-431 (water/acetone 6:4) contained 0.1 g of (S)-[1-[[[[[5-[[[4,5-bis(phenylmethoxy)-2-pyridinyl]-carbonyl]amino]-2-pyridinyl]amino]sulfonyl]amino]carbonyl]-2-oxo-3-azetidinyl]carbamic acid phenylmethyl ester. Melting point 176°-178° C. (dec.), white solid.

IR (KBr): 1790 cm$^{-1}$ CO $\beta$-lactam.

$^1$H-NMR (DMSO, 200 MHz): $\delta$=3.12-3.75 (m, 2H); 4.73 (m, 1H); 5.03 (s, 2H); 5.37 (s, 4H); 7.36 (m, 16H); 7.81 (2, 1H); 7.97 (d, 1H); 8.16 (d, 1H); 8.30 (s, 1H); 8.63 (d, 1H); 10.67 (s, 1H); ppm.

(C)
(S)-3-Amino-N-[[[5-[[1,4-dihydro-5-hydroxy-4-oxo-2-pyridinyl)carbonyl]amino]-2-pyridinyl]amino]sulfonyl]-2-oxo-1-azetidinecarboxamide, ditrifluoroacetate salt 1.5 g of (S)-[1-[[[[[5-[[[4,5-bis(phenylmethoxy)-2-pyridinyl]carbonyl]amino]-2-pyridinyl]amino]sulfonyl]amino]carbonyl]-2-oxo-3-azetidinyl]carbamic acid, phenylmethyl ester in 10 ml of trifluoroacetic acid and 2 ml of thioanisole were stirred for 18 hours at room temperature. 50 ml of ethyl acetate and 50 ml of ether were added and a white precipitate of (S)-3-amino-N-[[[5-[[1,4-dihydro-5-hydroxy-4-oxo-2-pyridinyl)carbonyl]amino]-2-pyridnyl]amino]sulfonyl]-2-oxo-1-azetidinecarboxamide, ditrifluoroacetate was obtained.

IR (KBr): 1790 cm$^{-1}$ CO $\beta$-lactam.

(D)
[3S(Z)]-2-[[[1-(2-Amino-4-thiazolyl)-2-[[1-[[[[5-[[(1,4-dihydro-5-hydroxy-4-oxo-2-pyridinyl)carbonyl]amino]-2-pyridinyl]amino]sulfonyl]amino]carbonyl]-2-oxo-3-azetidinyl]amino]-2-oxoethylidene]amino]oxy]-2-methylpropanoic acid, disodium salt To 1.38 g of (Z)-2-amino-$\alpha$-[[2-diphenylmethoxy)-1,1-dimethyl-2-oxoethoxy]imino]-4-thiazoleacetic acid suspended in 30 ml of acetonitrile was added at $-30°$ C. 1.34 ml of triethylamine followed by 0.71 ml of diphenylchlorophosphate in 10 ml of acetonitrile. After stirring for 1½ hours at $-30°$ C., a solution of 2.1 g of silylated (S)-3-amino-N-[[[5-[[1,4-dihydro-5-hydroxy-4-oxo-2-pyridinyl)carbonyl]amino]-2-pyridinyl]amino]sulfonyl]-2-oxo-1-azetidinecarboxamide, ditrifluoroacetate salt in 50 ml of acetonitrile (obtained after stirring 2.1 g of (S)-3-amino-N-[[[5-[[1,4-dihydro-5-hydroxy-4-oxo-2-pyridinyl)carbonyl]amino]-2-pyridinyl]amino]sulfonyl]-2-oxo-1-azetidinecarboxamide, 2.0 trifluoroacetate with 3.16 ml of bistrimethylsilylacetamide for 30 minutes, evaporation and redissolving the residue in 50 ml of acetonitrile) was added dropwise (ca. 20 minutes). The mixture was stirred for 1 hour at $-10°$ C. and 1 hour at 0° C. The solvent was distilled off in vacuo and the residue stirred in 100 ml of ice water and one drop of 2N hydrochloric acid for 1 hour. The precipitate was filtered off and washed with water. Yield: 3.1 g of crude [3S(Z)]-2-[[[-(2-amino-4-thiazolyl)-2-[[1-[[[[5--[[1,4-dihydro-5-hydroxy-4-oxo-2-pyridinyl)carbonyl]amino]-2-pyridinyl]amino]sulfonyl]amino]carbonyl]-2-oxo-3-azetidinyl]-amino]-2-oxoethylidene]amino]oxy]-2-methylpropanoic acid, diphenylmethyl ester after drying. This material was dissolved in 50 ml of tetrahydrofuran and 1.5 g of sodium-2-ethylhexanoate was added, followed by 50 ml of ether. 1.9 g of precipitate of crude [3S(Z)]-2-[[[1-(2-amino-4-thiazolyl)-2-[[1-[[[[-[5-[[(1,4-dihydro-5-hydroxy-4-oxo-2-pridinyl)carbonyl]amino]-2-pyridinyl]amino]sulfonyl]amino]carbonyl]-2-oxo-3-azetidinyl]amino]-2-oxoethylidene]amino]oxy]-2-methylpropanoic acid, diphenylmethyl ester was isolated by filtration, beige solid. Purification of this product by column chromatography on XAD-2 resin, water-/acetonitrile gradient (9:1→6:4) and combination of appropriate fractions yielded 0.4 g of material.

This material was dissolved in 10 ml of trifluoroacetic acid and 2 ml of anisole and stirred for 1 hour at $-10°$ C. After adding 40 ml of ether, 0.2 g of beige solid [3S(Z)]-2-[[[-(2-amino-4-thiazolyl)-2-[[1-[[[[5-[[1,4-dihydro-5-hydroxy-4-oxo-2-pyridinyl)carbonyl]amino]-2-pyridinyl]-amino]sulfonyl]amino]carbonyl]-2-oxo-3-azetidinyl]amino]-2-oxoethylidene]amino]oxy]-2-methylpropanoic acid, trifluoroacetate salt was obtained (crude).

The crude material was dissolved in 5 ml of water+3 ml of acetonitrile by adjusting the pH to 5.5 with sodium bicarbonate solution, filtering and chromatographing on a reverse phase Organogen column, water-/acetonitrile (9:1) as eluent to obtain 0.04 g of [3S(Z)-]-2-[[[1-(2-amino-4-thiazolyl)-2-[[1-[[[[5-[[(1,4-dihydro--5-hydroxy-4-oxo-2-pyridinyl]carbonyl]amino]-2-pyridinyl]amino]sulfonyl]amino]carbonyl]-2-oxo-3-azetidinyl]amino]-2-oxoethylidene]amino]oxy]-2methylpropanoic acid, disodium salt, melting point 270°-290° C. (dec.).

$^1$H-NMR (200 MHz): $\delta$=1.27 (s, 6H); 3.53 (m, 1H); 3.80 (m, 1H); 4.82 (m, 1H); 6.67 (s, 1H); 7.08 (d, 1H); 8.29 (d, 1H); ppm.

IR (KBr): 1790 cm$^{-1}$ CO $\beta$-lactam.

What is claimed is:

1. A compound having the formula

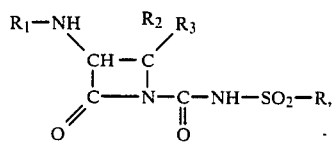

or a pharmaceutically acceptable salt thereof, wherein

R is 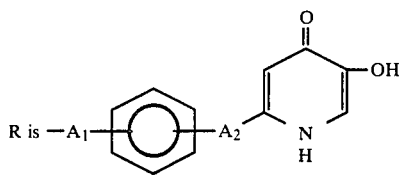

or

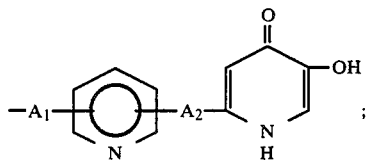

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered hetrocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl,

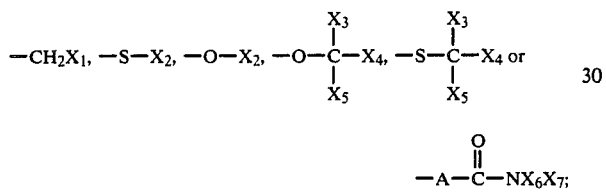

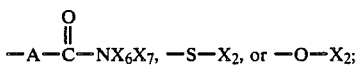

$X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano, $$-A-\overset{O}{\underset{\|}{C}}-NX_6X_7, -S-X_2, \text{ or } -O-X_2;$$

$X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

A is $-CH=CH-$, $-(CH_2)_m-$, $-(CH_2)_m-O-$, $-(CH_2)_m-NH-$ or $-CH_2-S-CH_2-$;

m is 0, 1 or 2;

$A_1$ is $-NH-$ or

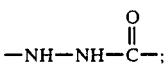

and $A_2$ is

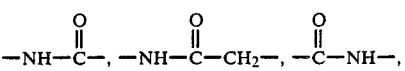

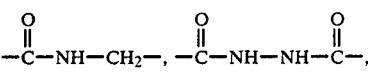

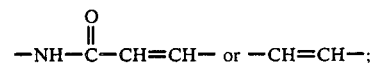

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, alkanoyloxy, aminocarbonyl, or carboxy groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 of 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "a 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "substituted amino" refers to a group having the formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein R is

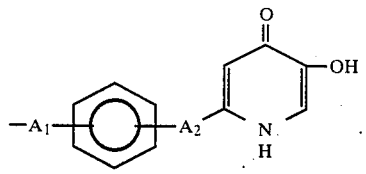

3. A compound in accordance with claim 1 wherein R is

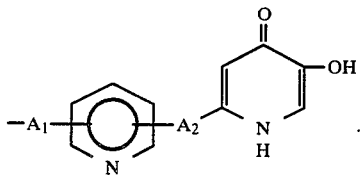

4. A compound in accordance with claim 2 wherein $A_1$ is —NH—.
5. A compound in accordance with claim 3 wherein $A_1$ is —NH—.
6. A compound in accordance with claim 2 wherein $A_1$ is

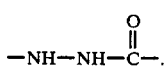

7. A compound in accordance with claim 3 wherein $A_1$ is

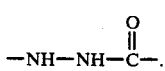

8. A compound in accordance with claim 2 wherein $A_2$ is

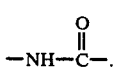

9. A compound in accordance with claim 2 wherein $A_2$ is

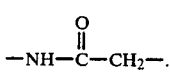

10. A compound in accordance with claim 2 wherein $A_2$ is

11. A compound in accordance with claim 2 wherein $A_2$ is

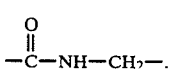

12. A compound in accordance with claim 2 wherein $A_2$ is

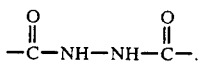

13. A compound in accordance with claim 2 wherein $A_2$ is

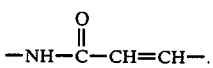

14. A compound in accordance with claim 2 wherein $A_2$ is —CH=CH—.
15. A compound in accordance with claim 3 wherein $A_2$ is

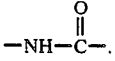

16. A compound in accordance with claim 3 wherein $A_2$ is

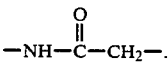

17. A compound in accordance with claim 3 wherein $A_2$ is

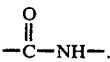

18. A compound in accordance with claim 3 wherein $A_2$ is

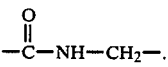

19. A compound in accordance with claim 3 wherein $A_2$ is

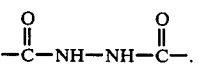

20. A compound in accordance with claim 3 wherein $A_2$ is

21. A compound in accordance with cliam 3 wherein $A_2$ is —CH=CH—.
22. A compound in accordance with claim 1 wherein $R_1$ is

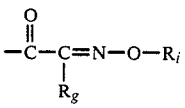

and $R_g$ is 2-amino-4-thiazolyl and $R_i$ is methyl, ethyl, carboxymethyl, 1-carboxy-1-methylethyl, 1-carboxy-1-ethyl, or

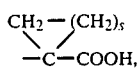

wherein s is 1, 2, or 3.

23. A compound in accordance with claim 1 wherein $R_1$ is

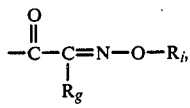

$R_g$ is 2-amino-4-thiazolyl- and $R_1$ is carboxymethyl, 1-carboxy-1-methylethyl, 1-carboxy-1-ethyl or

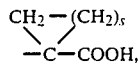

wherein s is 1, 2 or 3.

24. The compound in accordance with claim 1, [3S(-Z)]-2-[[[1-(2-amino-4-thiazolyl)-2-[[1-[[[[4-[[[(1,4-dihydro-5-hydroxy-4-oxo-2-pyridinyl)methyl]amino]carbonyl]phenyl]amino]sulfonyl]amino]carbonyl]-2-oxo-3-azetidinyl]amino]-2-oxoethylidene]amino]oxy]-2-methylpropanoic acid, or a pharmaceutically acceptable salt thereof.

25. The compound in accordance with claim 1, [3S(-Z)]-2-[[[1-(2-amino-4-thiazolyl)-2-[[1-[[[[5-[[(1,4-dihydro-5-hydroxy-4-oxo-2-pyridinyl)carbonyl]amino]-2-pyridinyl]amino]sulfonyl]amino]carbonyl]-2-oxo-3-azetidinyl]amino]-2-oxoethylidene]amino]oxy]-2-methylpropanoic acid, or a pharmaceutically acceptable salt thereof.

* * * * *